US010426530B2

(12) United States Patent
Humphreys

(10) Patent No.: US 10,426,530 B2
(45) Date of Patent: *Oct. 1, 2019

(54) RETAINING MECHANISM

(71) Applicant: Warsaw Orthopedic, Inc., Warsaw, IN (US)

(72) Inventor: Kevin R. Humphreys, Oxford, MS (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 707 days.

This patent is subject to a terminal disclaimer.

(21) Appl. No.: 15/091,240

(22) Filed: Apr. 5, 2016

(65) Prior Publication Data

US 2016/0213410 A1    Jul. 28, 2016

Related U.S. Application Data

(63) Continuation of application No. 14/551,741, filed on Nov. 24, 2014, now Pat. No. 9,326,803, which is a continuation of application No. 13/600,736, filed on Aug. 31, 2012, now Pat. No. 8,932,335.

(51) Int. Cl.
*A61B 17/80* (2006.01)
*A61B 17/70* (2006.01)
*A61B 17/00* (2006.01)

(52) U.S. Cl.
CPC ...... *A61B 17/8042* (2013.01); *A61B 17/7059* (2013.01); *A61B 17/808* (2013.01); *A61B 17/8038* (2013.01); *A61B 2017/00862* (2013.01)

(58) Field of Classification Search
CPC ................. A61B 17/8038; A61B 17/8042
See application file for complete search history.

(56) References Cited

U.S. PATENT DOCUMENTS

| 6,306,139 | B1 | 10/2001 | Fuentes |
| 7,306,605 | B2 | 12/2007 | Ross |
| 7,452,370 | B2* | 11/2008 | Anderson ..................... 606/296 |
| 7,727,266 | B2 | 6/2010 | Lindemann et al. |
| 7,833,226 | B2* | 11/2010 | Grabowski ........ A61B 17/7059 606/289 |
| 8,702,766 | B2* | 4/2014 | Mueller ............. A61B 17/8042 606/289 |
| 2012/0158068 | A1 | 6/2012 | Humphreys |
| 2013/0218211 | A1 | 8/2013 | Humphreys |

* cited by examiner

*Primary Examiner* — Andrew Yang

(57) ABSTRACT

A retaining mechanism for use in affixing a stratum to bone is disclosed. The mechanism comprises a stratum comprising a first surface, a second surface, and a hole extending between the two surfaces. The hole has a central longitudinal axis extending substantially perpendicular to the two surfaces. The retaining element comprises a first position that permits a fastener to be passed through the hole, a second position that at least partially overlaps the hole, and a spring element. The spring element is configured to engage the stratum, configured to move in a direction substantially perpendicular to the central longitudinal axis of the hole when the retaining element moves between its first and second positions, and configured to engage the retaining element to help maintain the retaining element in its second position to help prevent inadvertent backing out of the fastener after it has been fully inserted into the hole.

20 Claims, 8 Drawing Sheets

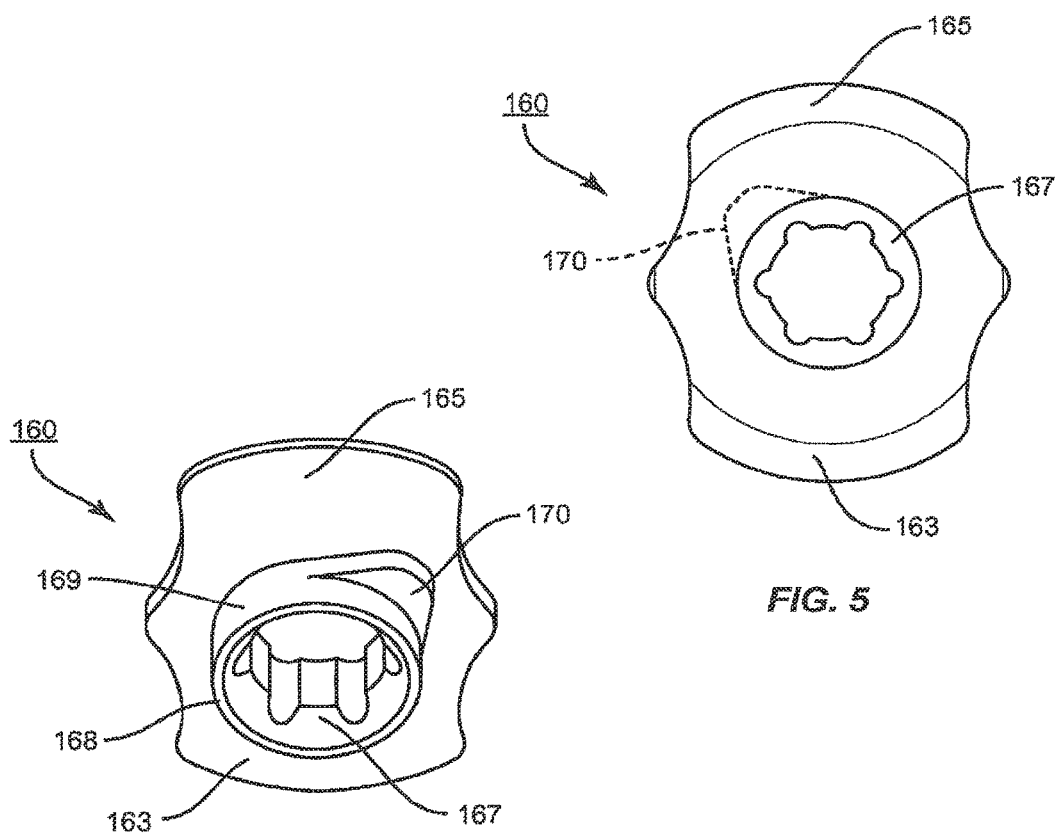
FIG. 5
FIG. 5A
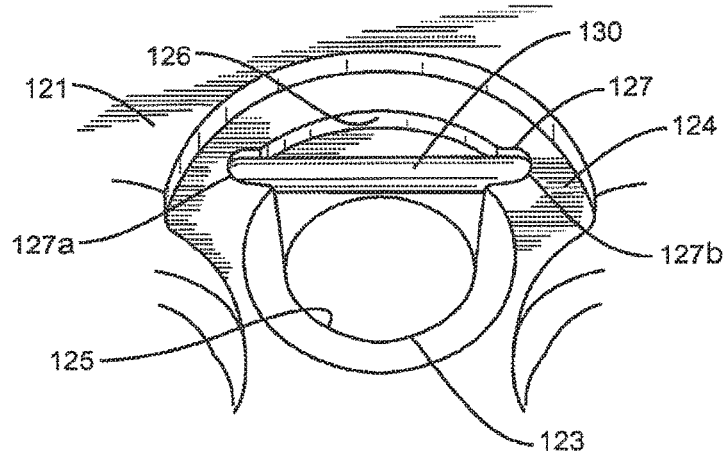
FIG. 6

RETAINING MECHANISM

The present application is a continuation application U.S. patent application Ser. No. 14/551,741, filed Nov. 24, 2014, which is a continuation of U.S. patent application Ser. No. 13/600,736, filed Aug. 31, 2012, now U.S. Pat. No. 8,932,335, which is related to commonly-owned U.S. patent application Ser. No. 12/970,130, filed Dec. 16, 2010, and entitled "Retaining Mechanism," which is now U.S. Pat. No. 8,454,667. The complete disclosure of each of these applications is incorporated herein by reference, in their entireties.

FIELD OF INVENTION

The present invention is directed to systems for affixing a stratum to bone.

BACKGROUND

The present disclosure relates to retaining mechanisms, and more particularly, systems for affixing a stratum to bone.

SUMMARY OF THE INVENTION

A retaining mechanism for use in affixing a stratum to bone is disclosed. The mechanism comprises a stratum comprising a first surface, a second surface, and a hole extending between the first surface and the second surface. The hole has a central longitudinal axis that extends substantially perpendicular to the first surface and the second surface, wherein the first surface is configured to engage at least a portion of the bone. The retaining element comprises a first position that permits a fastener to be passed through the hole, a second position that at least partially overlaps the hole, and a spring element. The spring element is configured to engage the stratum, configured to move in a direction substantially perpendicular to the central longitudinal axis of the hole when the retaining element moves between its first and second positions, and configured to engage the retaining element such that the spring element helps maintain the retaining element in its second position so as to help prevent inadvertent backing out of the fastener after the fastener has been fully inserted into the hole.

Further, a system for affixing stratum to bone is disclosed. The system comprises a retaining mechanism and at least one fastener configured to pass through the hole in the stratum and engage the bone.

BRIEF DESCRIPTION OF THE DRAWINGS

FIG. 5 is an isometric top view of the retaining element of FIG. 1;

FIG. 5A is an isometric bottom view of the retaining element of FIG. 1;

FIG. 6 is a cut-away, isometric top view of the stratum of FIG. 1;

DETAILED DESCRIPTION

Figure 1:
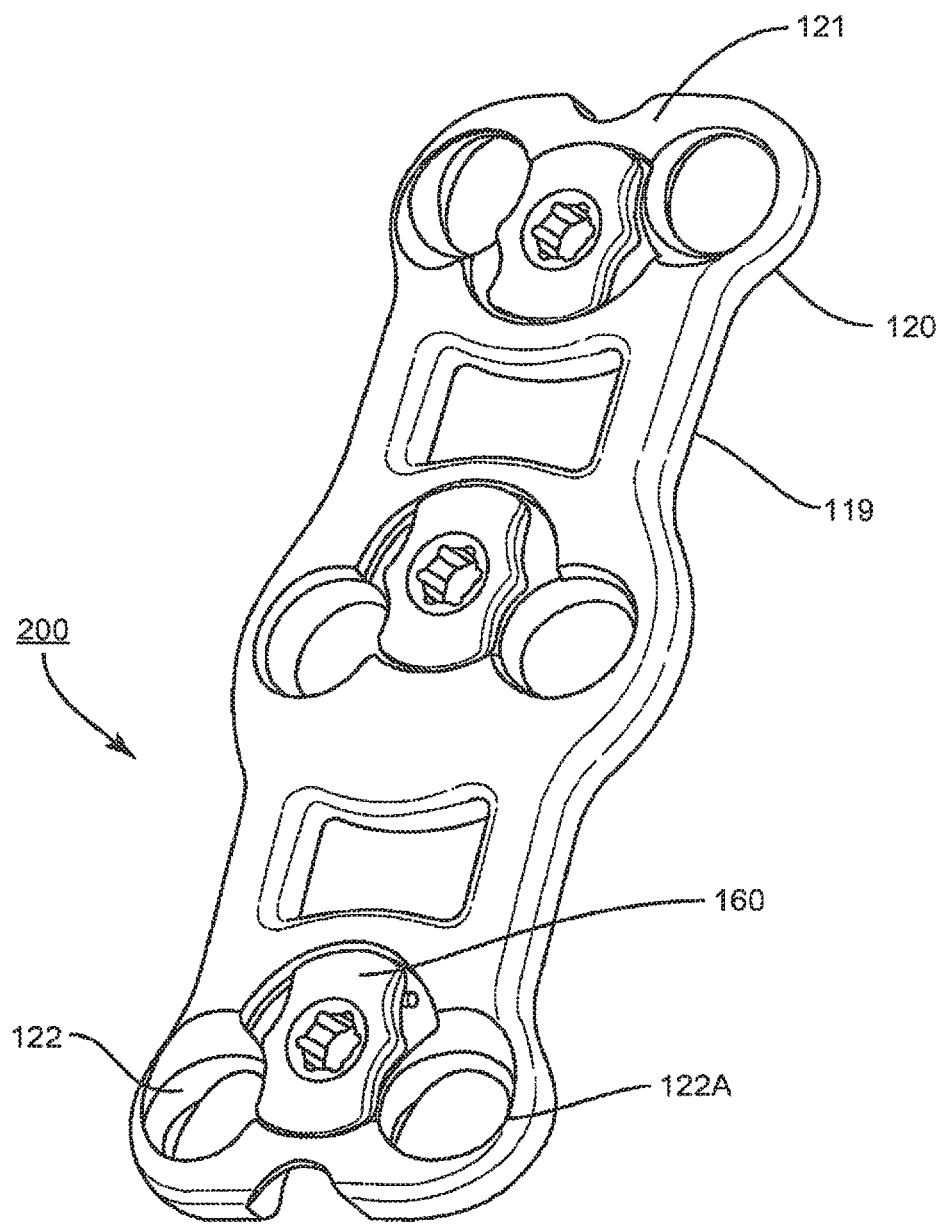
FIG. 1 is an isometric top view of a retaining mechanism for affixing a stratum to bone.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 shows an isometric top view of a retaining mechanism 200 for affixing a stratum 120 to bone, for example, to two or more levels of vertebral bodies. As shown in FIG. 1, the stratum 120 is designed for connecting three vertebral bodies (not shown), each vertebral body receiving two fasteners, one fastener through each hole, for example, holes 122 and 122A. As shown in FIG. 1, the stratum 120 may be, for example, a spinal plate for connecting cervical vertebrae by affixing the stratum 120 to the anterior surface of the vertebrae. Further, as shown in the Figures and as described herein, the fasteners may be, for example, screws.

The retaining mechanism 200 comprises a stratum 120, a retaining element 160 and a spring element 130. The stratum 120 comprises a first surface 119, a second surface 121, and six holes (for example, holes 122 and 122A) extending between the first surface 119 and the second surface 121. As shown in FIG. 1, the first surface 119 is configured to engage at least a portion of the bone. The retaining element 160 comprises a first position that permits a fastener to be passed through the hole (for example, hole 122 or 122A), a second position that at least partially overlaps the hole (for example, hole 122 or 122A), and a spring element 130 configured to engage the stratum 120 and configured to engage the retaining element 160 such that the spring element 130 helps maintain the retaining element 160 in its second position so as to help prevent inadvertent backing out of the fastener after the fastener has been fully inserted into the hole (for example, hole 122 or 122A). Note that, as shown in FIG. 1, the stratum contains three retaining mechanisms. One is retaining mechanism 200 and the other two are similar, with each mechanism configured for another bone or bone segment, for example, configured for separate vertebral bodies. Further, note that hole 122 has a central longitudinal axis that extends substantially perpendicular to the first and second surfaces 119 and 121 of the stratum 120, respectively. Further, the other holes are similarly situated.

Figure 2:
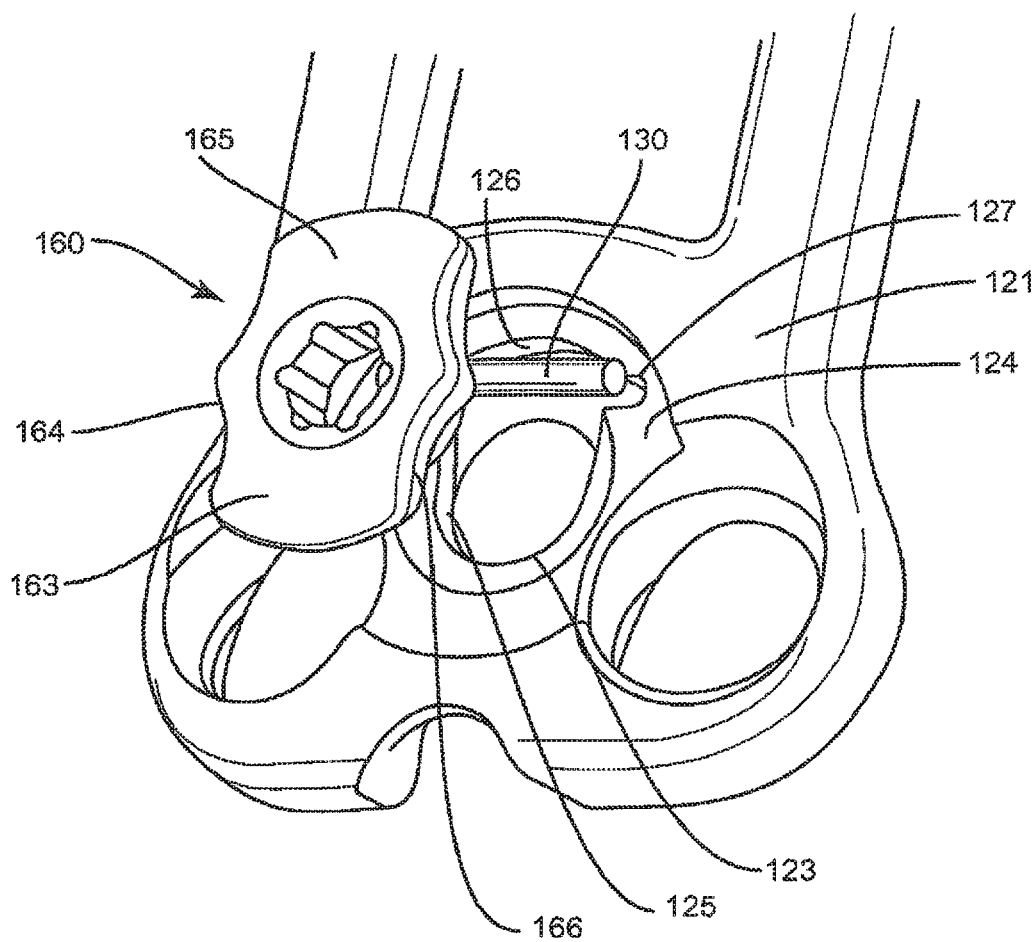
FIG. 2 is a cut-away, exploded, isometric top view of retaining mechanism of FIG. 1.

FIG. 2 shows a cut-away, exploded, isometric top view of retaining mechanism 200 of FIG. 1. As shown in FIG. 2, the stratum 120 is further configured to engage the retaining element 160. As shown in FIG. 2, the second surface 121 of the stratum 120 comprises a first recess 124 configured to engage the retaining element 160. Further, as shown in FIG. 2, the first recess 124 comprises a second recess 126 configured to engage the spring element 130, and more specifically, to accommodate movement of the spring element 130 when the retaining element 160 moves between its first and second positions. Yet further, as shown in FIG. 2, the first recess 124 further comprises a third recess 127 configured to engage the spring element 130, and more specifically, to maintain engagement between the spring element 130 and the stratum 120.

As shown in FIG. 2, the first recess 124 is situated in a plane that is substantially parallel to the second surface 121 of the stratum 120. Further, the second surface 121 of the stratum 120 is substantially parallel to the first surface 119 of the stratum 120. As shown in FIG. 2, the stratum 120 has a central hole 123 that extends between the first recess 124 and the second surface of the stratum 120, and that extends in a direction substantially perpendicular to the first recess 124 and the second surface of the stratum 120. As shown in FIG. 2, the central hole 123 comprises a sidewall 125 and the second recess 126 extends radially from the central hole 123, which is in a direction substantially parallel to the second surface 121. Further, as shown in FIG. 2, the third recess 127 extends from the second recess 126 and in a plane that is substantially parallel to the second surface 121.

In addition, as shown in FIG. 2, the retaining element 160 further comprises a first cut-out 164 and a second cut-out 166 on one end of the retaining element 160. On the opposite end of the retaining element 160, there is another pair of cut-outs (not marked) that are similar to the first and second cut-outs 164 and 166. In addition, as shown in FIG. 2, situated between the first and second cut-outs 164 and 166, there is a first leg 163 of the retaining element 160. Further, as shown in FIG. 2, there is a second leg 165 on the opposite end of the retaining element 160. Note that the first and second legs 163 and 165 of the retaining element 160 are situated in a plane that is substantially parallel to each of the first and second surfaces 119 and 121 of the stratum 120.

Figure 3:
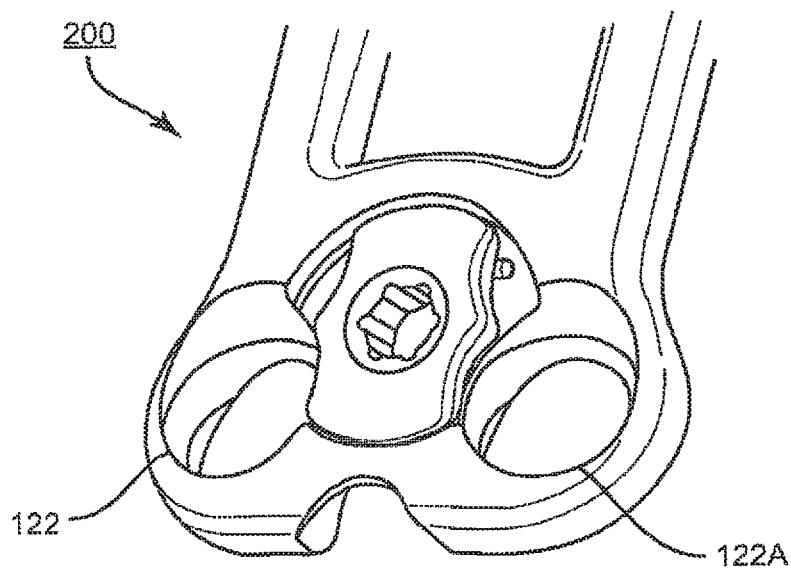
FIG. 3 is a cut-away, isometric top view of e retaining mechanism of FIG. 1.

FIG. 3 shows a cut-away, isometric top view of the retaining mechanism 200 of FIG. 1. As shown in FIG. 3, the retaining element 160 is in its first position, which permits a fastener to be passed through the hole 122 or 122A.

Figure 4:
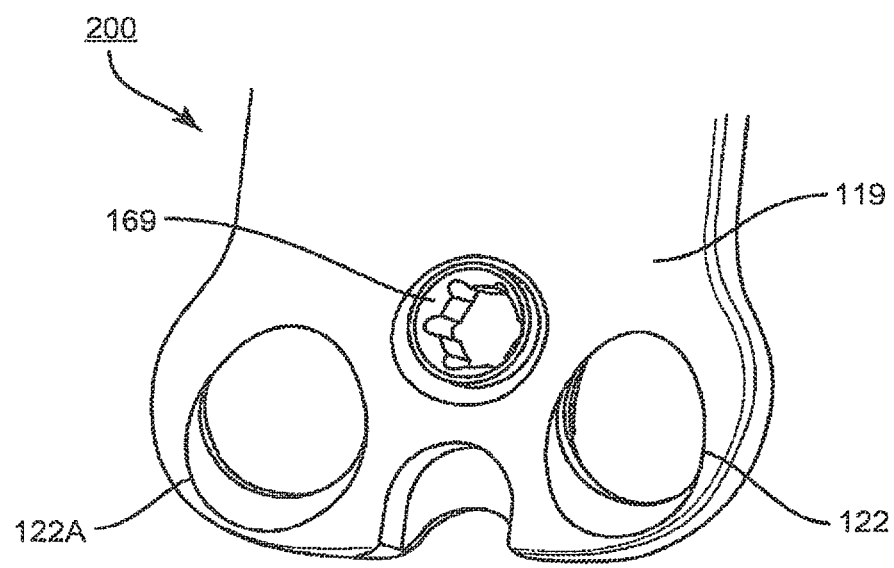
FIG. 4 is a cut-away, isometric bottom view of the retaining mechanism of FIG. 1.

FIG. 4 shows a cut-away, isometric bottom view of the retaining mechanism 200 of FIG. 1. As shown in FIG. 4, the retaining element 160 further comprises a grommet portion 169 situated between holes 122 and 122A. The grommet portion 169 helps the retaining element 160 maintain position affixed to the stratum 120, but also allows the retaining element 160 to rotate, for example, between its first position and its second position.

FIG. 5 shows an isometric top view of the retaining element 160 of FIG. 1. As shown in FIG. 5, a cam 170 or projection of material 170 is visible in phantom lines (as well as in some other figures) because it is situated on the underside of the retaining element 160. Further, FIG. 5 also shows the first leg 163 and the second leg 165 of the retaining element 160. Note that the cam 170 extends and lies in a plane that is substantially parallel to the legs 163 and 165 of the retaining element 160.

FIG. 5A shows an isometric bottom view of the retaining element 160 of FIG. 1. As shown in FIGS. 5 and 5A, the retaining element 160 further comprises a central shaft 167 that is configured to pass through the stratum 120. As shown in FIGS. 5 and 5A, at least the top of the central shaft 167 has a hexagonal shape. Also, as shown, the central shaft 167 defines a hole through the retaining element 160 and is situated at or near the center of the retaining element 160. As shown, the retaining element 160 may be rotated by, for example, inserting a hexagonal-shaped end of a tool into the central shaft 167 to thereby rotate the retaining element 160 from, for example, its first position to its second position, or vice versa. Note that the central shaft 167 (and corresponding tool) need not have a hexagonal-shape, but may be one of a variety of shapes so long as the function of rotating the retaining element 160 can be accomplished. For example, other polygonal shapes such as a square would suffice.

As shown in FIG. 5A, the central shaft 167 has a first portion 168 and a second portion 169. The first portion 168 of the central shaft 167 is adjacent the grommet portion 169 and the first surface 119 (or bottom) of the stratum 120. The second portion 169 of the central shaft 167 is adjacent the second leg 165 of the retaining element 160 and the second surface 121 (or top) of the stratum 120. As shown in FIG. 5A, the cam 170 of retaining element 160 is situated on and extends from the second portion 169 of the central shaft 167. As shown in FIG. 5A, the cam 170 is substantially triangular in shape or substantially beak-shaped projection of material, i.e., projecting from the central shaft 167.

FIG. 6 shows a cut-away, isometric top view of the stratum 120 of FIG. 1. FIG. 6 shows an enlarged view of the first recess 124, the second recess 126, the third recess 127 and the spring element 130. As shown in FIG. 6, the third recess 127 has a first end 127a and a second end 127b. Further, as shown in FIG. 6, the stratum 20 further comprises a central hole 123 configured to receive the central shaft 167 of the retaining element 160. As shown in FIG. 6, the central hole 123 is situated in a plane that is substantially perpendicular to the plane in which the first recess 124 lies.

With reference to the figures, when the retaining element 160 is rotated, e.g., from the first position to the second position, the cam 170 rotates and imparts a force against the spring element 130. The ends of the spring element 130 are held in position in the ends 127a and 127b of the third recess 127 and when the cam 170 rotates and contacts the spring element 130, the spring element 130 flexes and moves into a portion of or all of the second recess 126. Note that the spring element 130 moves in a direction substantially parallel to the second surface, and substantially parallel to the first recess 124, which also is substantially perpendicular to the central hole 123 of the stratum 120.

As shown in FIG. 6, the second recess has an arcuate shape to accommodate the spring element 130 when it is flexed by the cam 170. More specifically, when the retaining element 130 is in its first position to allow for insertion of fasteners through holes 122 and 122A of the stratum 120, the cam 170 is situated closer to the first end 127a of the third recess 127 than the second end 127b. The resting state of the spring element 130 is that as shown in FIG. 6. Thus, when the retaining element 130 is in its first position, the spring element 130 helps maintain the retaining element 130 in its first position. When a surgeon (or other person) wishes to prevent inadvertent backing out of fasteners from the stratum 120, the retaining element 130 is rotated approximately ¼ turn (approximately 90 degrees) in the clockwise direction and must overcome the force of the spring element 130. Similarly, when the retaining element 130 is in its second position, the cam 170 is situated closer to the second end 127b of the third recess than the first end 127b and the spring element 130 helps maintain the retaining element 130 in its second position.

Note that the cam 170 need not be substantially triangular in shape or substantially beak-shaped but its shape may vary as long as the function of maintaining the retaining element 130 in its first and second positions, and allowing movement between the two positions, is accomplished. For example, a frusto-conical shape or more hemispherical shape or other polygonal shape may work as well. Similarly, note that the second recess 126 need not have an arcuate shape, but may vary as long as the function of allowing room for the spring element 130 to move (or flex) when the retaining element 130 moves between its first position and its second position is accomplished. For example, the second recess 126 may be more rectangular or some other polygonal shape may work as well.

Figure 7:
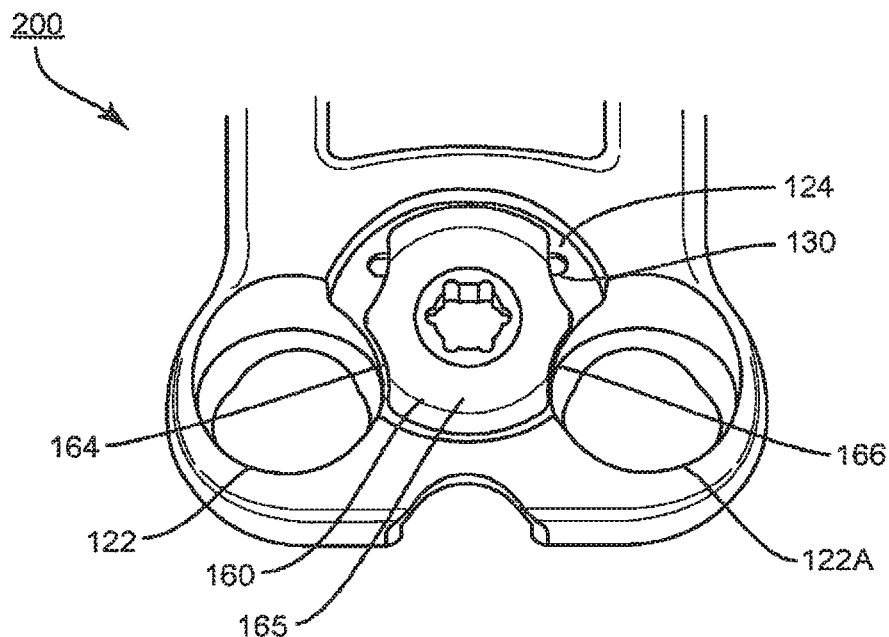
FIG. 7 is a cut-away, isometric top view of the retaining mechanism of FIG. 1.

FIG. 7 shows a cut-away, isometric top view of the retaining mechanism 200 of FIG. 1. Specifically, FIG. 7 shows an enlarged view of the area surrounding the retaining element 160 when it is in its first position. As shown in FIG. 7, when the retaining element 160 is in its first position, the first cut-out 164 and the second cut-out 166 of the retaining element 160 permit first and second fasteners to be passed through the first and second holes 122 and 122A of the stratum 120, respectively. Further, as shown in FIG. 7, when the retaining element 160 is in its first position, the cam 170 on the underside of the retaining element 160 engages the spring element 130. In this way, the cam 170 helps maintain the retaining element 160 in its first position.

Figure 8:
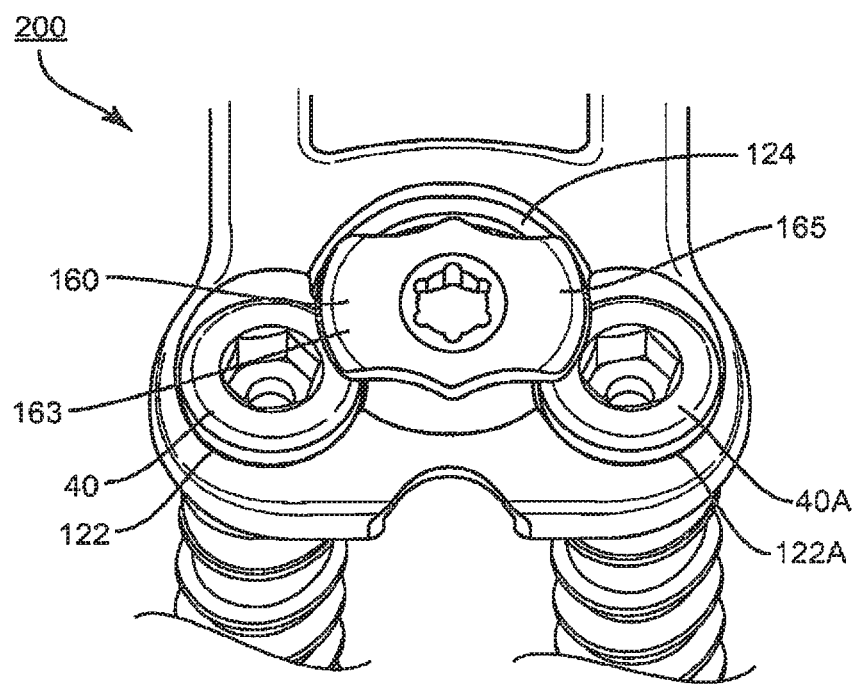
FIG. 8 is another cut-away, isometric top view of the retaining mechanism of FIG. 1.

FIG. 8 shows another cut-away, isometric top view of the retaining mechanism 200 of FIG. 1. Specifically, FIG. 8 shows an enlarged view of the area surrounding the retaining element 160 when it is in its second position. As shown in FIG. 8, a first fastener 40 and a second fastener 40A has already been fully inserted into the first and second holes 122 and 122A of the stratum 120, respectively. Further, as shown in FIG. 8, after the fasteners 40 and 40A have been fully inserted, the retaining element 160 has been rotated in the clockwise direction approximately ¼ turn from its position of FIG. 7. During rotation of the retaining element 160, the cam 170 presses against the spring element 130 and the spring element 130 flexes, allowing the cam 170 and retaining element 160 to rotate to its second position—as shown in FIG. 8. Note that when the spring element 130 flexes, the middle portion of the spring element (i.e., that portion not situated and held in place in the ends 127a and 127b of the third recess 127) temporarily moves into the space provided by the second recess 126. As shown in FIG. 8, the when the retaining element 160 is in its second position, the first leg 163 and the second leg 165 of the retaining element 160 partially overlap the first and second holes 122 and 122A of the stratum 120, respectively, so as to prevent inadvertent backing out of fasteners 40 and 40A. Further, as shown in FIG. 8, when the retaining element 160 is in its second position, the cam 170 engages the spring element 130 so as to help maintain the retaining element 160 in its second position. When the retaining element 160 is in its second position, the spring element 130 is less stressed than when the retaining element 160 rotates between its first and second positions, but applies enough pressure against the cam 170 to help maintain the retaining element 160 in its second position.

Figure 9:
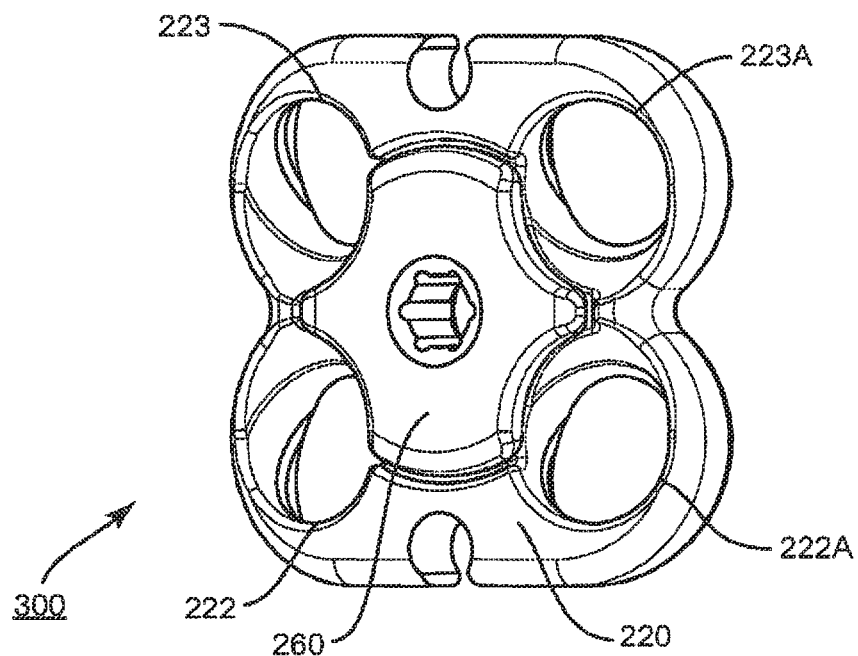
FIG. 9 is an isometric top view of another embodiment of a retaining mechanism for affixing a stratum to bone.

FIG. 9 shows an isometric top view of another embodiment of a retaining mechanism for affixing a stratum to bone. Specifically, FIG. 9 shows a retaining mechanism 300 for affixing a stratum 220 to a single level of vertebrae, i.e., to connect two adjacent vertebral bodies. By comparison, the stratum 220 of FIG. 1 is used to connect three vertebral bodies (two levels of vertebrae). As shown in FIG. 9, the stratum 220 has four holes, with each vertebral body receiving two fasteners, one fastener through each hole, for example, holes 222, 222A, 223 and 223A. Further, the retaining mechanism 300 comprises a retaining element 260, which has a different shape than retaining element 160.

Figure 10:
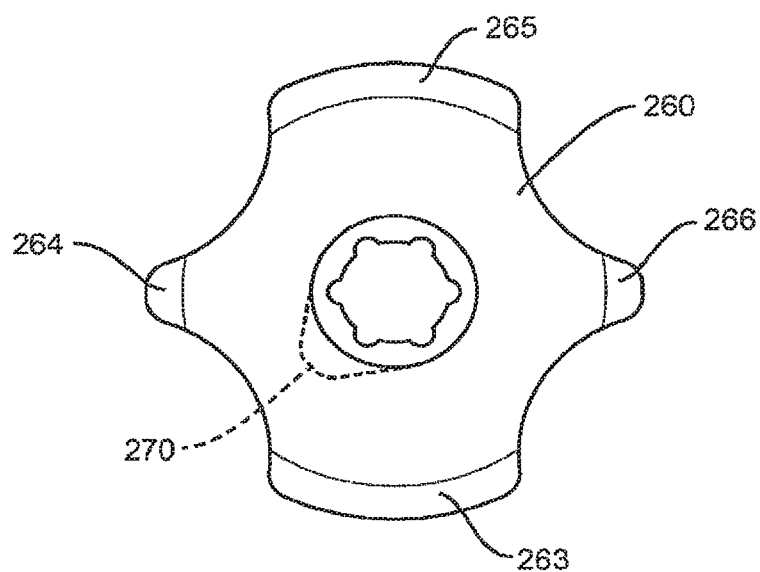
FIG. 10 is a top view of the retaining element of FIG. 9.

FIG. 10 shows a top view of the retaining element 160 of FIG. 9. As shown in FIG. 10, a cam 270 is visible in phantom lines because it is situated on the underside of the retaining element 260. Further, FIG. 10 shows that retaining element 260 has four legs, where two legs are larger than the other two legs. Specifically, legs 263 and 265 are similar in shape and they are larger than legs 234 and 266, which themselves are similar in shape. As with retaining mechanism element 160, the cam 270 of retaining element 260 extends and lies in a plane that is substantially parallel to the legs 263, 265, 264 and 266.

Figure 11:
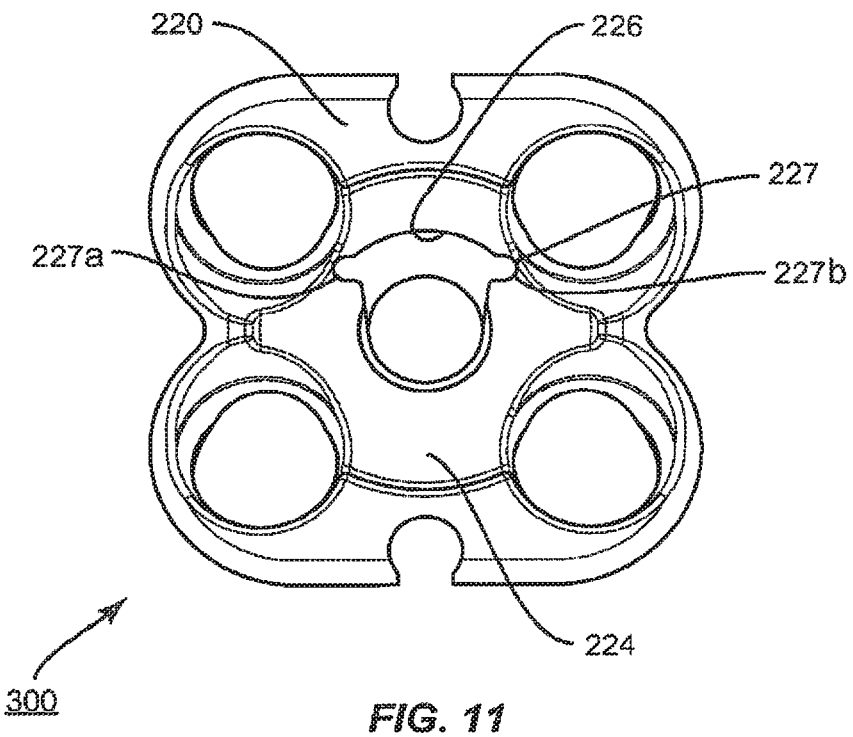
FIG. 11 is another top view of the retaining mechanism of FIG. 9.

FIG. 11 shows another top view of the retaining mechanism 300 of FIG. 9. Note, however, that FIG. 11 does not show the retaining element 260 and does not show a spring element (230 shown in FIGS. 12 and 12A). As shown in FIG. 11, the stratum 220 comprises a first recess 224, a second recess 226 and a third recess 227, all of which serve similar functions as the recesses of the stratum 120 of retaining mechanism 200. Further, as shown in FIG. 11, the third recess 227 comprises ends 227a and 227b, which are configured to engage the spring element 230, and more specifically, to maintain engagement between the spring element 230 and the stratum 220.

Figure 12:
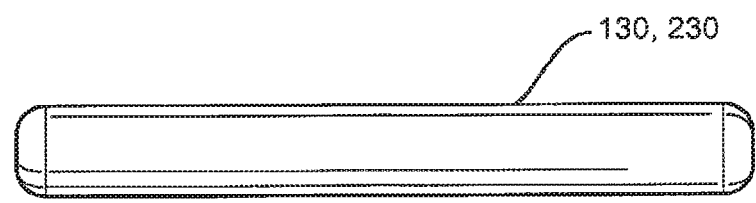
FIG. 12 is a top view of a spring element.
Figure 12A:
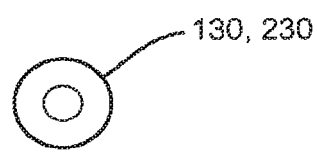
FIG. 12A is a side view of a spring element.

FIG. 12 shows a top view of a spring element such as 130 for use with retaining mechanism 200, or a spring element such as 230 for use with retaining mechanism 300. FIG. 12A shows a side view of the spring element 130, 230 of FIG. 12. As shown in FIGS. 12 and 12A, the spring elements 130 and 230 each have a substantially cylindrical shape or that of a rod having a circular cross section.

Figure 13:
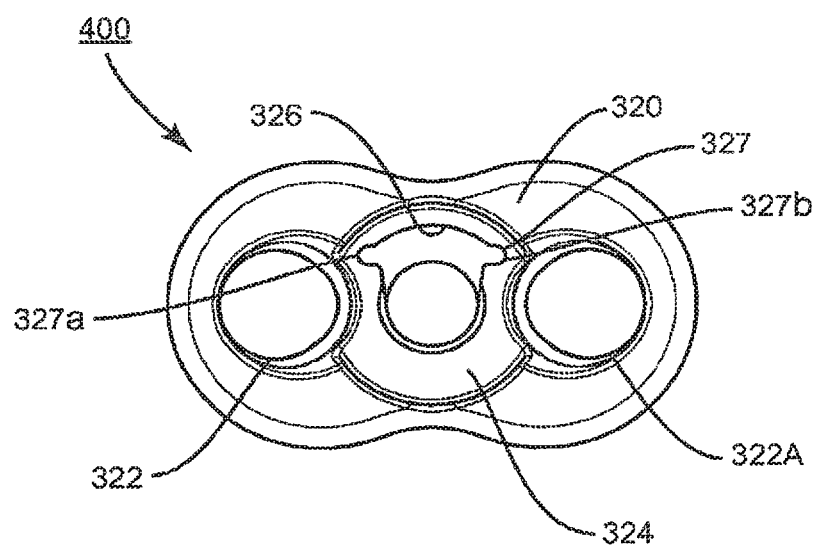
FIG. 13 is a top view of another embodiment of a retaining mechanism for affixing a stratum to bone.

FIG. 13 shows a top view of another embodiment of a retaining mechanism 400 for affixing a stratum to bone. Specifically, FIG. 13 shows a retaining mechanism 400 (retaining element 360 shown in FIG. 14) for affixing a stratum 320 to a single level of vertebrae, i.e., to connect two adjacent vertebral bodies. As shown in FIG. 13, the stratum 320 has only two holes 322 and 322A, one hole 322 for one vertebral body and the other hole 322A for the adjacent vertebral body. Specifically, hole 322 is configured to receive a fastener that engages with one vertebral body, and hole 322A is configured to receive another fastener that engages with an adjacent vertebral body.

As shown in FIG. 13, note that the figure does not show the retaining element 360 and does not show a spring element. The spring element intended to work with the retaining mechanism 400 would be similar in function and shape to the spring element 230 shown in FIGS. 12 and 12A. As shown in FIG. 13, the stratum 320 comprises a first recess 324, a second recess 326 and a third recess 327, all of which serve similar functions as the recesses of the stratum 120 of retaining mechanism 200. Further, as shown in FIG. 13, the third recess 327 comprises ends 327a and 327b, which are configured to engage the spring element, and more specifically, to maintain engagement between the spring element and the stratum 320. Note that stratum 320 need not be limited to connected two adjacent vertebrae, but may be designed to connect more than two vertebrae such that each level of vertebrae would have a single hole for receiving a single fastener.

Figure 14:
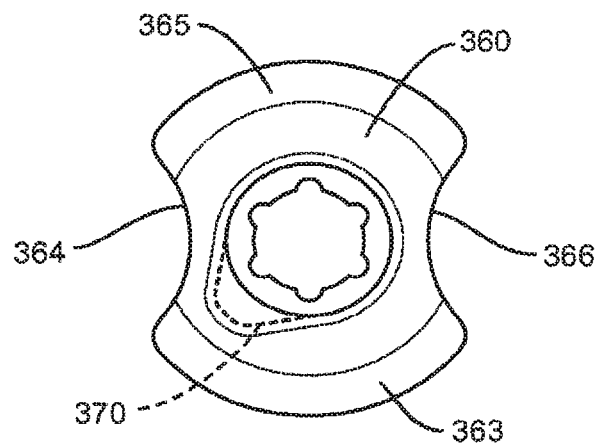
FIG. 14 is a top view of the retaining element to be used with the retaining mechanism of FIG. 13.

FIG. 14 shows a top view of the retaining element 360 to be used with the retaining mechanism 400 of FIG. 13. Specifically, the retaining element 360 is configured to be positioned in the first recess 324. As shown in FIG. 14, a cam 370 is visible in phantom lines because it is situated on the underside of the retaining element 360. Further, FIG. 14 shows that retaining element 360 has two legs 363 and 365. Specifically, situated between legs 263 and 265 are cut outs 364 and 366. As with retaining mechanism element 160, the cam 370 of retaining element 260 extends and lies in a plane that is substantially parallel to the legs 363 and 365.

Parts of the retaining mechanisms 200, 300 and/or 400 may have a variety of shapes and sizes and still accomplish the functions described herein. For example, the shape of the retaining elements 160, 260 and/or 360 or any of its constituent parts may be different than that shown in the Figures as long as they accomplish their respective functions described herein. The retaining elements 160, 260 and/or 360 may be any shape as long as it allows for insertion of fasteners and helps prevent inadvertent backing out of the fasteners after the fasteners have been fully inserted into the holes (for example, hole 122 or 122A).

In the embodiments shown and described herein, the retaining elements 160, 260 and/or 360 are substantially rigid. Further, in the embodiments shown and described herein, each stratum 120 (or 220 or 320) is substantially rigid. Accordingly, the recesses 124, 126 and 127 (or 224, 226 and 227, or 324, 326 and 327) therein are substantially rigid.

The term "substantially" as used herein may be applied to modify any quantitative representation which could permissibly vary without resulting in a change in the basic function to which it is related. For example, the retaining element 160 may be considered substantially rigid if when the retaining element 160 is in its second position, the retaining element 160 at least partially overlaps a hole 122 or 122A so as to help prevent inadvertent backing out of a fastener after the fastener has been fully inserted into the hole.

In the embodiments described herein, a stratum may be made of a variety of biocompatible materials (metal or non-metal), including but not limited to, Titanium Alloys, commercially available Titanium, stainless steel, polyetheretherketone ("PEEK"), cobalt chrome ("CoCr"), polyetherketoneketone ("PEEK"), ultra high molecular weight polyethylene ("UHMWPE"), polyethylene, shape memory metals, other polymers or any combination of such materials. Similarly, the retaining mechanisms 160, 260 and 360 and/or the fasteners (for example, fastener 40) may be made of the same materials. Also, any suitable materials know in the art may work for each of these elements as well as for other elements described herein.

In the embodiments shown, the spring elements 130, 230 (or that used with retaining mechanism 400) have elastic properties. Thus, each spring element 130, 230 comprises a material that has elastic properties. For example, each spring element 130, 230 may comprise a material such as metal that is elastic. In addition, each spring element 130, 230 (as examples) may be made of Nickel Titanium (NiTi), commercially pure Titanium, a Titanium alloy or any combination of such materials. Further, as noted, the spring elements 130, 260 may have shapes other than substantially cylindrical. That is, the spring elements 130, 260 may take any form that satisfies its function described herein, for example, being able to adequately engage with the retaining elements 160 (or 260) and the stratum 120 (or 220) and being able to sufficiently maintain the retaining element 160 (or 260) in its second position so as to not allow the fasteners (for example, fastener 40) to inadvertently back out of the stratum 120 (or 220). For example, although the spring element 130 (or 230) is shown as having a substantially cylindrical shape or that of a rod having a circular cross section, a variety of shapes may be employed. For example, a rod or member having a more rectangular or cross section of a square may work as well.

All adjustments and alternatives described above are intended to be included within the scope of the invention, as defined exclusively in the following claims. Those skilled in the art also should realize that such modifications and equivalent constructions or methods do not depart from the spirit and scope of the present disclosure, and that they may make various changes, substitutions, and alterations herein without departing from the spirit and scope of the present disclosure. Furthermore, as used herein, the terms components and modules may be interchanged. It is understood that all spatial references, such as "superior," "inferior," "anterior," "posterior," "outer," "inner," "upper," "underside," "top," "bottom," and "perimeter" are for illustrative purposes only and can be varied within the scope of the disclosure.

The invention claimed is:

1. A retaining mechanism comprising:
    a plate comprising a hole;
    a retaining element comprising a body including a cutout, the retaining element being rotatable relative to the plate between a first position in which the cutout is aligned with the hole to permit a fastener to be passed through the hole and a second position in which the body at least partially overlaps the hole; and
    a resilient element positioned between the plate and the retaining element, wherein the resilient element is a spring having a linear configuration.

2. A retaining mechanism as recited in claim 1, wherein the resilient element is configured to engage the retaining element to help maintain the retaining element in the first position and the second position.

3. A retaining mechanism as recited in claim 1, wherein the resilient element is less stressed when the retaining element is in the second position than when the retaining element moves between the first and second positions.

4. A retaining mechanism as recited in claim 1, wherein the resilient element applies pressure against the retaining element when the retaining element is in the second position.

5. A retaining mechanism as recited in claim 1, wherein the resilient element is in a resting state when the retaining element is in the first position, wherein the resilient element is linear when in the resting state.

6. A retaining mechanism as recited in claim 1, wherein the resilient element and the retaining element are positioned within a first cavity when the retaining element is in the first and second positions, and wherein the resilient element is positioned in a second cavity that is in communication with the first cavity when the retaining element is in the second position, wherein the resilient element is linear when in the resting state.

7. A retaining mechanism comprising:
    a plate comprising a first hole and a second hole that is spaced apart from the first hole; and
    a retaining element comprising a body, a first cutout and a second cutout that is spaced apart from the first cutout, the retaining element being rotatable relative to the plate between a first position in which the first cutout is aligned with the first hole and the second cutout is aligned with the second hole to permit a fastener to be passed through each of the first and second holes and a second position in which the body at least partially overlaps the first hole and the second hole, wherein the plate comprises a third hole situated between the first and second holes, the third hole having a grommet disposed therein, the retaining element engaging the grommet to rotate the retaining portion about an axis that extends substantially perpendicular to the first and second holes.

8. A retaining mechanism as recited in claim 7, wherein the third hole extends through the first and second surfaces, a portion the retaining element being rotatably positioned within the third hole.

9. A retaining mechanism as recited in claim 7, wherein a shaft of the retaining element is rotatably positioned within the third hole, the shaft extending from the body of the retaining element.

10. A retaining mechanism as recited in claim 7, further comprising a resilient element positioned between the plate and the retaining element, the resilient element being configured to engage the retaining element to help maintain the retaining element in the first position and the second position.

11. A retaining mechanism as recited in claim 10, wherein the resilient element is less stressed when the retaining element is in the second position than when the retaining element moves between the first and second positions.

12. A retaining mechanism as recited in claim 10, wherein the resilient element applies pressure against the retaining element when the retaining element is in the second position.

13. A retaining mechanism as recited in claim 10, wherein the resilient element is a spring.

14. A retaining mechanism as recited in claim 10, wherein the resilient element is a spring having a linear configuration.

15. A retaining mechanism as recited in claim 7, wherein the grommet is monolithically formed with the body.

16. A retaining mechanism as recited in claim 7, wherein the retaining element comprises a shaft extending from the body, an outer surface of the shaft defining the grommet.

17. A retaining mechanism as recited in claim 7, wherein the retaining element comprises a shaft extending from the body, an outer surface of the shaft defining the grommet, a cam of the retaining element extending from an outer surface of the shaft, the cam being configured to maintain the retaining element in the first position.

18. A retaining mechanism comprising:
    a plate comprising a hole that extends through opposite top and bottom surfaces of the plate;
    a retaining element comprising a body including a cutout, the retaining element being rotatable relative to the plate between a first position in which the cutout is aligned with the hole to permit a fastener to be passed through the hole and a second position in which the body at least partially overlaps the hole; and
    a resilient element positioned between the plate and the retaining element, the resilient element being configured to engage the retaining element to help maintain the retaining element in the first position and the second position.

19. A retaining mechanism as recited in claim 18, wherein the plate comprises a second hole that extends through the first and second surfaces, the second hole having a grommet disposed therein, the retaining element engaging the grommet to rotate the retaining element about an axis that extends substantially perpendicular to the first and second surfaces.

20. A retaining mechanism as recited in claim 18, wherein the plate comprises a recess defined by a third surface of the plate, the resilient element being positioned within the recess, the third surface being substantially parallel with the first and second surfaces and positioned between the first and second surfaces, a bottom surface of the body engaging the third surface.

* * * * *